US008872811B1

(12) United States Patent
Rump et al.

(10) Patent No.: US 8,872,811 B1
(45) Date of Patent: Oct. 28, 2014

(54) VISUALIZATION METHOD

(71) Applicants: Martin Rump, Winterscheid (DE);
Marc S. Ellens, Grand Rapids, MI (US);
Adrian Kohlbrenner, Thalwil (CH);
Francis Lamy, Wollerau (CH); Beat Frick, Buchs (CH)

(72) Inventors: Martin Rump, Winterscheid (DE);
Marc S. Ellens, Grand Rapids, MI (US);
Adrian Kohlbrenner, Thalwil (CH);
Francis Lamy, Wollerau (CH); Beat Frick, Buchs (CH)

(73) Assignee: X-Rite Switzerland GmbH, Regensdorf (CH)

( * ) Notice: Subject to any disclaimer, the term of this patent is extended or adjusted under 35 U.S.C. 154(b) by 0 days.

(21) Appl. No.: 14/095,435

(22) Filed: Dec. 3, 2013

Related U.S. Application Data

(63) Continuation of application No. 13/953,285, filed on Jul. 29, 2013.

(51) Int. Cl.
*G06T 1/00* (2006.01)
*G06F 17/50* (2006.01)

(52) U.S. Cl.
CPC ................... *G06F 17/5009* (2013.01)
USPC .......................................... 345/418; 345/582

(58) Field of Classification Search
USPC .................................. 345/418, 582
See application file for complete search history.

(56) References Cited

PUBLICATIONS

Cook et al., A Reflectance Model for Computer Graphics, ACM Transactions on Graphics, vol. 1, No. 1, Jan. 1982, pp. 7-24.
Kajiya, The Rendering Equation, ACM, vol. 20, No. 4., 1986, pp. 143-150.
Rusinkiewicz, A New Change of Variables for Efficient, Sanford University, 1998, pp. 1-12.
Daubert, et al., Efficient Cloth Modeling and Rendering, author associated with the University of British Columbia, 2001, pp. 1-9.
McAllister et al., Efficient Rendering of Spatial Bi-Directional Reflectance Distribution Functions, The Eurographics Association, 2002, pp. 79-88 and 157.
Lawrence, et al., Inverse Shade Trees for Non-Parametric Material Representation and Editing, authors associated with Princeton University, Columbia University and MERL, 2006, pp. 735-745.
Kautz, et al., Interactive Editing and Modeling of Bidirectional Texture Functions, to appear at the ACM SIGGRAPH conference proceedings, 2007, pp. 1-10.
Rump, et al., Photo-Realistic Rendering of Metallic Car Paint from Image-Based Measurements, Eurographics, 2008, pp. 1-10.
Guthe, et al., BTF-CIELab: A Perceptual Difference Measure for Quality Assessment and Compression of BTFs, Computer Graphics Forum, vol. 28, No. 1, 2008, pp. 101-113.
An, et al., AppProp: All-Pairs Appearance-Space Edit Propagation, author associated with Darmouth College, 2008, pp. 1-9.
Xu, et al., Edit Propagation on Bidirectional Texture Functions, Pacific Graphics, 2009, pp. 1-7.
Rump, et al., Efficient Resampling, Compression and Rendering of Metallic and Pearlescent Paint, VMV, 2009, pp. 1-8.
An, et al., AppWarp: Retargeting Measured Materials of Appearance-Space Warping, authors associated with Darmouth College, Microsoft Research Asia and Sapienza University of Rome, 2011, pp. 1-9.
Alldrin, et al., Photometric Stereo With Non-Parametric and Spatially-Varying Reflectance, authors associated with the University of California, San Diego and Harvard Univeristy, no date, pp. 1-8, 2008.
U.S. Appl. No. 13/953,285, filed Jul. 29, 2013.

*Primary Examiner* — Maurice L McDowell, Jr.
(74) *Attorney, Agent, or Firm* — McCarter & English, LLP

(57) ABSTRACT

The present invention provides a method of digitally generating, via the use of a computer, data indicative of a synthesized appearance of a simulated material having physically plausible appearance attributes. The method includes determining a set of data indicative of the synthesized appearance of the simulated material based at least in part on data associated with the physically tangible source material and at least in part on data of measured attributes of the physically tangible reference material.

28 Claims, 5 Drawing Sheets

VISUALIZATION METHOD

RELATED APPLICATIONS

This application is a continuation application that claims priority to U.S. Non-Provisional application Ser. No. 13/953,285, filed Jul. 29, 2013, the entire disclosures of which are expressly incorporated by reference.

BACKGROUND

The present invention relates to the general field of visualization of materials or surfaces on a monitor by using computer graphic techniques. In general, a digital representation of a real material or surface is rendered, mapped onto a target object of arbitrary shape, and the simulated appearance of the target object is then visualized under user selected illumination conditions and viewing directions.

From the start, it should be understood that the field of this invention is not image creation or manipulation, which typically includes only 2- and 3-dimensions and does not require that the result resemble reality, much less be renderable in reality. The field here is visualization of simulated materials that are renderable in reality—they are physically plausible materials.

Getting an accurate visualization of a simulated appearance is, for most materials and surfaces occurring in the real world, an extremely challenging technological problem. Consequently, much effort has been expended on finding approximations that are both of aesthetically pleasing appearance and quickly computed, albeit without concern that the resultant appearance is representative of a material that is physically plausible, such as required by a product designer.

Further, in creative applications like product design, large databases of materials are required. Various functions have been developed, such as the Bidirectional Texture Function (BTF), which is a material representation fitting a large number of complex materials of many different types. However, to measure a sufficiently representative BTF for a given real material requires relatively complex measuring equipment and the measurements are very time consuming. A representative surface area of the material must be measured pixel by pixel for a large number of illumination directions and viewing directions, typically by using a number of digital color cameras and a complex illumination system with hundreds of spot-type lamps distributed over the hemisphere above the material being measured.

With the BTF measured, the visualization itself, i.e. the graphical representation of the material on the monitor under any desired illumination condition and any desired viewing direction and applied or mapped to any object of any shape, is realized by digital rendering techniques which use the BTF database as input data. Suitable rendering techniques and software are well known in the computer graphics art and are not subject of the present invention. Such rendering techniques or software can retrieve color reflectance values from the BTF database for each given pixel of the real material for each given illumination direction and for each given viewing direction. Intermediate values can be calculated by interpolation from the actual values stored in the BTF database.

Unfortunately, the creation of such databases usually containing thousands of materials requires substantial technical effort both in terms of measurement time and device sophistication and is therefore often not practicable and often prohibitively expensive.

As an alternative to producing databases for a large number of individual materials a set of basis materials with corresponding BTFs might be provided from which the designer can chose a sample and then modify or edit the BTF on-the-fly to meet his requirements. Here, an intuitive and fast editing approach is necessary to maintain efficiency in the creative process. Moreover, the goal of the editing process is to generate physically plausible results that represent simulated materials that may be manufactured.

One common approach is to fit analytical reflectance models to the data (McAllister 2002, Daubed 2001) and to perform a modification of model parameters afterwards. For efficient parameter changes additional methods might be used which simplify propagation of parameters across the material surface (An 2008). While using reflectance models guarantees physical plausibility to a certain degree, manually finding new parameters to match a desired target appearance is a tedious task. Moreover, this approach is limited to materials that can be faithfully described by simple reflectance models. Most complex materials, especially those exhibiting special features like glittering or significant and large surface structures, cannot be reproduced by such an approach with high accuracy.

Other methods do not rely on analytical models but modify reflectance data in a more direct way. Lawrence 2006 used inverse shade trees and an optimization scheme coined ACLS to decompose the spatially varying material properties of planar samples from dense hemispherical samplings in a collection of 1D curves and 2D textures. This approach factorized the material into multiple, low-dimensional parts, which could be edited separately, causing certain reflectance changes on the whole material when reconstructing from the factorized representation. While this approach allows for a high-accuracy representation of the source material, editing of the single parts still remains a manual process and a desired target appearance is therefore difficult to achieve. Moreover, the method is only applicable for flat materials.

In Kautz 2007 a first set of editing operators for generic BTF data was proposed. While those operators can deal with arbitrarily complex materials, their heuristic nature means that the physical plausibility of the final result may be low. Additionally, a given target material is very difficult to match as the operator parameters have to be specified manually.

A combination of the edit propagation algorithm (An 2008) and the editing operators defined in Kautz 2007 was made by Xu 2009. While this simplifies the usage of the edit operators, it does not overcome the basic problems of physical implausibility and manual work.

Using measured reflectance on both the source and target side of the editing process was proposed in An 2011. This algorithm can transfer reflectance data from one material to match the spatial reflectance distribution of a second material allowing for very intuitive editing with minimal manual effort. While the method allows enrichment of sparsely captured representations (even single images) with highly detailed reflectance data, the other way around is not possible as the edited material is always represented by reflectance samples from the target material.

There is a need to easily and quickly develop a synthesized appearance of a simulated material that not only "looks good," but is physically plausible to enable product designers to evaluate a wide range of simulated materials, knowing that any material selected by the designer from the range of materials is physically plausible for making real world products.

SUMMARY

The present invention provides a method of digitally generating, via the use of a computer, data indicative of a synthesized appearance of a simulated material having physically plausible appearance attributes.

The present invention provides a method for the visualization of real materials that doesn't require individually measured BTF databases for all individual materials to be visualized and thus considerably reduces the amount of pre-captured BTF data.

The present invention also provides a data set of values of appearance attributes for a synthesized appearance of a simulated material having physically plausible appearance attributes generated by the method of the present invention.

In some embodiments, the present invention also provides an image generated from a data set of values of appearance attributes for a synthesized appearance of a simulated material having physically plausible appearance attributes generated by the method of the present invention.

In some embodiments, the present invention also provides a system for digitally generating data indicative of a synthesized appearance of a simulated material having physically plausible appearance attributes.

DESCRIPTION OF EMBODIMENTS

Figure 1:
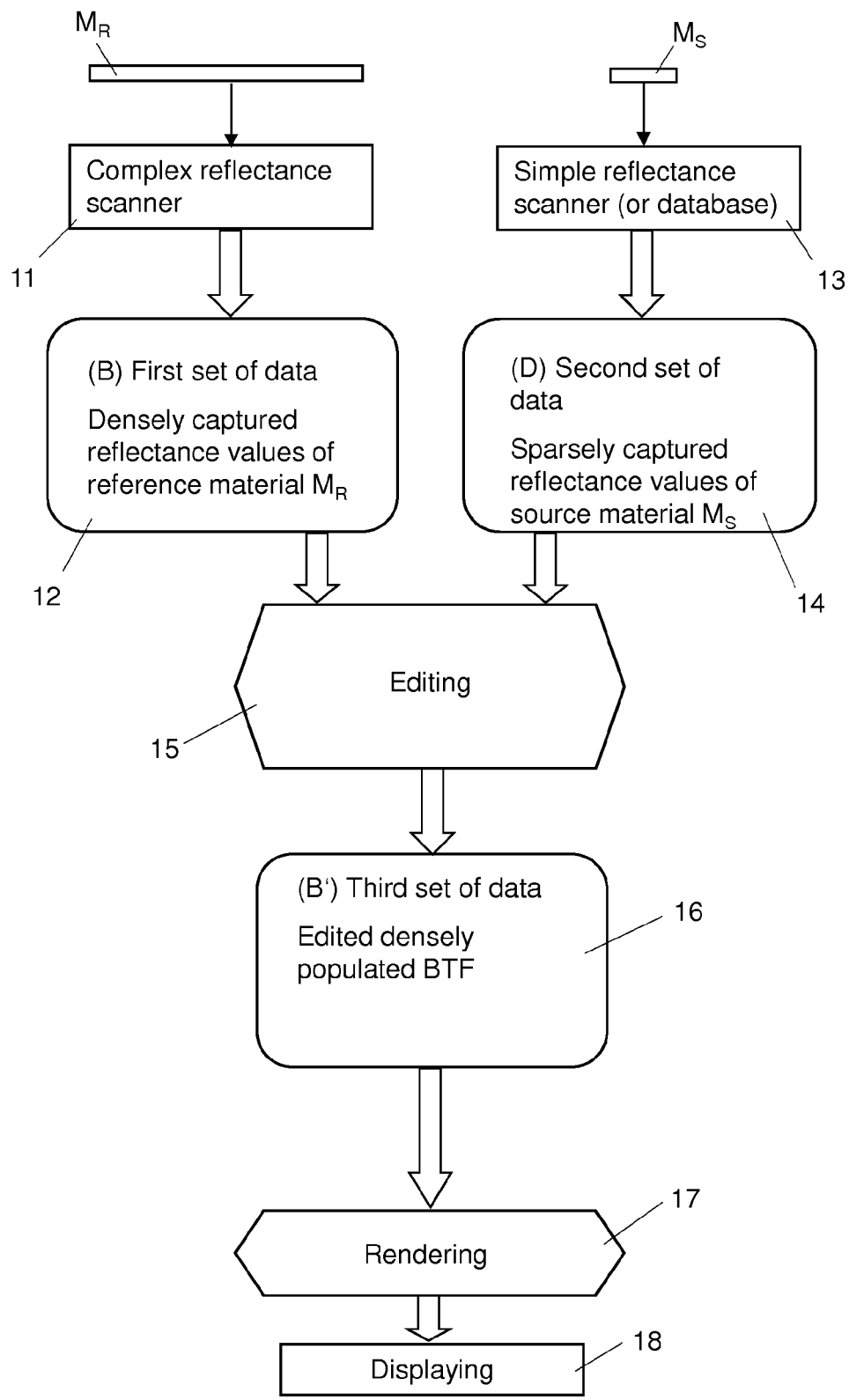
FIG. 1 is a flow diagram of one embodiment of the inventive method.

The following abbreviations are used herein:

BTF denotes a Bidirectional Texture Function or database. The BTF is a six dimensional function containing a color reflectance value (e.g. but not necessarily RGB) for every point (pixel) on a surface area of the material (2 spatial dimensions, i.e. x,y-coordinates) as well as for a large number of viewing and illumination directions (2*2 spatial direction dimensions, i.e. 2 elevation and 2 azimuth angles). Due to its discrete nature the BTF is a collection of data or database rather than a continuous function in the strict mathematical sense. In the following the terms BTF, BTF function and BTF database will be used synonymously.

B denotes a (densely populated) BTF measured for a reference material also referred to as target material. For each pixel of the measured area of the reference material and for a large number of illumination and viewing directions B holds a set of reflectance values which can be e.g. RGB color values or spectral values. In the following sets of reflectance values will be referred to shortly as reflectance values or color values.

D denotes the totality of sparsely captured reflectance values of one measuring point or spot of a source material (i.e., a material other than the reference or target material). The sparsely captured reflectance values D actually consist of a single set or a plurality of sets of e.g. RGB values or other color values or spectral values. If the source material is measured under one specific illumination condition and in one specific viewing direction only a single set of reflectance values results. If the source material is measured under several illumination directions and/or viewing directions a plurality s of sets Ds results according to the number of combinations of illumination and viewing directions. A typical color measuring device suitable for capturing sparse reflectance values is a portable multi-angle spectrophotometer such as the device MA98 of X-Rite, Inc., Grand Rapids, Mich., USA. This device features multi-angle illumination and multi-angle measuring light pick-up and produces 19 sets of reflectance values for each measuring spot. In the following sets of reflectance values will be referred to simply as reflectance values or color values. A measuring device for capturing said sparse reflectance values is referred to hereinafter also as a simple scanner. For the sake of completeness it is to be mentioned that the reflectance values D may also be taken, in practical use, from a database or from a suitable color chart or the like.

B' denotes a (densely populated) BTF database derived from B by modifying the original BTF B with sparse reflectance values D. Modifying a BTF is also referred to as editing a BTF. The modified BTF B' represents a simulated material that combines appearance properties of both the reference material and the source material.

As reflectance values D will be transferred to B, the reflectance values D have to be of the same type as those of B, i.e. RGB color values or spectral values or any other suitable color values. Otherwise either the reflectance values of B or preferably those of D have to be converted correspondingly.

The following definitions are used herein:

"Synthesized appearance" means an appearance which is generated from the appearance attributes of both the source and reference materials. It need not have identical size or format to either reference or source materials. The synthesized appearance will look more like the reference material than the source material. Suitable appearance attributes include, for example, lightness, saturation, texture, color, hue, gloss, specularity, distinctness of image, haze, subsurface scattering, turbidity, translucency, surface height variation and normal maps, etc.

"Reference material" means a material which has been extensively measured to densely populate a data set of a plurality of appearance attributes.

"Source material" means a material which has been measured to sparsely populate a data set of one or more appearance attributes. In some embodiments, the source and reference materials are related (e.g. both may have one or more of the same appearance attributes such as gloss, surface, color, etc.). In other instances, they may differ (i.e. they may have no similar appearance attributes).

"Physically plausible" means that the simulated material is typically capable of being created in the physical, real world. The term "Physically plausible" is used in contrast to that of "physically feasible." A "physically feasible" appearance is one that one can imagine constructing physically, but the real-world construction of such materials may not be possible. The present invention enables creation of physically plausible simulated materials because the first and second data sets are physically measured from tangible source and reference materials.

FIG. 1 shows one embodiment of the method according to the invention. Data is acquired for both the source and reference materials.

A sufficiently large surface area of a reference material $M_R$ is measured using a complex reflectance scanner (11) to provide a set of reflectance values for each pixel of the scanned surface area under a large number of illumination directions (at least 5, more preferably at least 10) and a large number of viewing directions (at least 5, more preferably at least 10).

The result is a first set of data indicative of the values of measured appearance attributes of the $M_R$. This first set of data is also referred to herein as the densely populated original BTF database B (12) for the $M_R$.

In some embodiments, the first set of data constitutes a Bidirectional Texture Function (BTF), a Bi-Directional Scattering-Surface Reflectance Distribution Function (BSSRDF), Spatially Varying Bi-Directional Transmission Distribution Function (SVBTDF), or a Spatially Varying Bi-Directional Reflectance Distribution Function (SVBRDF).

A measuring spot of a source material $M_S$ is measured using a simple reflectance scanner or color measuring device (13) to provide sparse reflectance values D (14). The result is a second set of data indicative of a value of at least one measured appearance attribute of the $M_S$. The appearance attribute of the $M_S$ includes at least one, but not all, of the appearance attributes measured on the $M_R$. The second set of data is also referred to herein as the "sparsely populated" data set. "Sparse" means less than at least 50% the amount in the densely populated BTF database B for the $M_R$. In some embodiments, the number of appearance attributes in the data collected from the $M_S$ is less than 1% of the number of appearance attributes represented in the BTF of the $M_R$.

The data acquisition steps are known per se and can be implemented by any suitable measurement equipment (including, for example, a spectrophotometer). The materials can be illuminated with electromagnetic (EM) radiation in the range of near IR, UV or humanly detectable frequency spectra.

The BTF data B can be acquired at the same time or a different time than the BTF data B' for the $M_S$. The BTF data B for the $M_R$ can be stored on the same computer or different computer used to store the data from the $M_S$.

Next, a third set of data indicative of the synthesized appearance of the simulated material is determined based at least in part on data from the second set of data associated with the $M_S$ and at least in part on data from the first set of data associated with the $M_R$. In some embodiments, the original BTF B of the $M_R$ is edited (modified) by transferring the sparse reflectance values D of the $M_S$ into the BTF B (15). In this editing step, a modified BTF B' is produced which is populated as densely as B but has reflectance values that make B' resemble the source material $M_S$, i.e. the reflectance values of B' are as similar as possible to reflectance values which would have been obtained if the BTF of the source material had been actually measured. The method of the present invention results in a third set of data indicative of physically plausible appearance attributes.

In some embodiments, the third set of data is determined based at least in part from data from the first and second data as well as data from a fourth set of data indicative of standardized values of appearance attributes representative of a family of generally similar physically tangible materials of which the reference material or the source material is a member.

The third set of data can be corrected to increase its physical plausibility. In some embodiments, an error value is used to correct the data. In some embodiments, the error value consists of (a) the difference between a parameter of a measured appearance attribute of the source material and the same parameter of the corresponding appearance attribute in the third set of data and (b) a physical plausibility value based on the difference between at least one, preferably at least two, parameter(s) of between at least one, preferably at least two, measured appearance attribute(s) of the reference material and the same parameter(s) of the corresponding measured appearance attribute(s) in the third set of data. In some embodiments, if the error value is greater than a predetermined threshold, then the third set of data is revised until the error value is less than the predetermined threshold value.

The third set of data may optionally be processed to form an image representative of the synthesized appearance of the simulated material. In some embodiments, the image may be 3-dimensional. FIG. 1 shows the third set of data (e.g., the edited BTF B') (16) can be fed as input data to a conventional rendering engine (17) and visualized on a display (18). Rendering and displaying a BTF are known in the art and are not subjects of the present invention per se.

The present invention also provides a data set of values of appearance attributes for a synthesized appearance of a simulated material having physically plausible appearance attributes generated by the method of the present invention.

The present invention also provides an image generated from a data set of values of appearance attributes for a synthesized appearance of a simulated material having physically plausible appearance attributes generated by the method of the present invention.

The present invention also provides a system for digitally generating data indicative of a synthesized appearance of simulated material having physically plausible appearance attributes, with the synthesized appearance being based on a physically tangible reference material and at least one value of a selected appearance attribute of a physically tangible source material different from the reference material.

In some embodiments, the system comprises (a) memory for storing a first set of data indicative of the values of measured appearance attributes of the reference material, with the measured appearance attributes being measured at a plurality of locations on the reference material and for a plurality of illumination directions or a plurality of viewing directions relative to each of the locations; (b) an instrument for measuring at least one appearance attribute of the source material and generating a second set of data indicative of a value of the measured appearance attribute, wherein the appearance attribute of the source material includes at least one, but not all, of the appearance attributes being measured on the reference material; and (c) a computer configured to receive the first and second sets of data and configured to determine a third set of data indicative of the synthesized appearance of the simulated material based at least in part on data from the second set of data associated with the physically tangible source material and at least in part on data from the first set of data of measured attributes of the physically tangible reference material different from that of the second set of data.

In some embodiments, the system further includes a processor configured to receive data from the third set of data and configured either (i) to form an image representative of the synthesized appearance of the simulated material based at least in part on the data from the third set of data or (ii) to produce an object having the synthesized appearance of the simulated material based at least in part on the data from the third set of data.

In some embodiments, the image representative of the synthesized appearance is two- or three-dimensional. In some embodiments, the third set of data is used to print a physically tangible object having the synthesized appearance of the simulated material. In some embodiments, the printed object is two- or three-dimensional. In some embodiments, third set of data to form a haptic display representative of the synthesized appearance of the simulated material. In some embodiments, at least a portion of the memory for storing the first set of data is carried on the computer.

In some embodiments, the computer and the instrument are combined in a single integral device. In some embodiments, the computer and the processor are combined in a single integral device.

In some embodiments, data from the first and second sets of data are transmitted via media selected from the group consisting of a hardware connection, a wireless connection or a portable memory device.

In some embodiments, the instrument constitutes a first instrument comprising at least one source of EM radiation in the range of near IR, UV or humanly detectable frequency spectra. In some embodiments, the instrument source emits the full spectra of EM radiation in the range of near IR, UV and humanly detectable frequency spectra. In some embodiments, the instrument source emits a selected spectrum of EM radiation from near IR, UV and visible EM frequencies.

In some embodiments, the first instrument further comprises at least one detector for measuring EM radiation reflected from or transmitted through the source material when illuminated by the source of EM radiation, and determining values of the appearance attributes of the source material.

In some embodiments, the system further comprises a second instrument for measuring appearance attributes of the physically tangible reference material at a plurality of locations on the reference material by illuminating each of the locations on the reference material with EM radiation in the range of near IR, UV or visible EM frequencies from a plurality of illumination directions and measuring the EM radiation reflected from or transmitted through the reference material from a plurality of viewing directions, and determining values of the appearance attributes of the reference material based on the reflected or transmitted EM radiation for data of the first set of data.

The methods, images and systems of the present invention can be used to bring variety, sophistication and accuracy to the virtual world. Designers, 3D artists, material specifiers and marketers can use the inventions described herein to visualize their designs with unmatched realism, using digital information measured from real materials. The present methodology enables the characterization of the full appearance of materials used in computer-aided design. Materials which can be simulated using the present invention include, but are not limited to, flooring materials (wood, concrete, vinyl, carpets, etc.), building materials (siding, shingles, etc.), paints (especially automotive), textiles (silks, hand-made fabrics, rugs, etc.), etc.

EXAMPLE

Embodiments will now be further described with reference to the following non-limiting Example. It should be understood that this Example, while indicating embodiments, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims. All documents referenced herein are incorporated by reference.

For an easier understanding, a simple practical example will make clear the goal of the invention. Assume a designer wishes to know what different designs of upholstery would look like in a real car. He has a relatively large variety of individual seat cover materials that are all made of the same textile fabric and, therefore, have the same or at least a very similar surface structure. The only difference between the individual materials may consist in their color patterns. All materials may have colored spots. One particular material may have white spots, another one may have red spots, a third one may have green spots, and so on. To visualize all these individual materials on a computer monitor according to the present invention only one of the materials needs to be densely scanned to produce a full reference BTF. The BTFs for the remaining materials can then be generated on the fly from the reference BTF by editing or modifying whereby the editing procedure requires information on which pixels of the material to be visualized are different and in what aspect (e.g. color) they are different from the reference material. Accordingly, the first, preparatory step of the editing procedure is to select those pixels of the source material $M_S$ that are different from the respective pixels of the reference material $M_R$, or in other words to select the pixels of which the corresponding reflectance values are to be edited (shortly pixels to be edited).

Theoretically, the pixels to be edited could be specified manually via their spatial coordinates. This, however, would be rather tedious, particularly if a large number of pixels are involved. Therefore, a software-assisted procedure is used as outlined in FIG. 2.

Selecting a pixel means that it is assigned a non-zero weight so that it is fully or at least partly considered in subsequent calculations. Pixels with zero weight are not considered in subsequent calculations. The weights build a selection mask.

In a first step of the pixel selection procedure one image of the scanned surface of the reference material $M_R$ is displayed on a computer monitor using a subset of data of the BTF B (21). The user then has to mark in the image displayed a surface region he wants to edit later, e.g. a spot of a certain color (22). Marking can be performed manually or by any suitably designed interactive routine known in the art.

Afterwards all similar surface regions can be located either manually or by applying an algorithm (such as, e.g., the AppProp algorithm described in An 2008, incorporated herein by reference in its entirety) (23). The AppProp algorithm works on the basis of self-similarities and calculates the weights so that all similar regions on the whole material surface get a high weight equal to or near one and all other regions receive a low weight equal to or near zero.

The AppProp algorithm is based on the minimization of an error function to propagate weights for selected pixels along similar appearance, leading to an intuitive continuation of selection. In some embodiments of the present invention, all weights of a set of pixels below a certain threshold are set to zero, i.e. only pixels with non-zero weights pertain to the set of pixels to be edited and will be considered for further calculations (24).

This optional modifying procedure of the inventive method needs to know what the selected pixels to be edited should finally look like. This information is provided by the sparse reflection values D captured from the corresponding measuring spot of the source material $M_S$.

The modifying procedure basically comprises an optimization procedure that minimizes an error function E(B'). This error function measures two different kinds of errors: a first part measures the (appearance) difference between a simulated material represented by the modified BTF B' and the sparse reflectance values D of the source material and a second part measures the (appearance) difference between the reference material as represented by its BTF B and the simulated material represented by the modified BTF B'. The first error part makes the edited (simulated) material look like the source material and the second error part ensures minimal deviation of the edited (simulated) material from the known reference material, therefore ensuring physical plausibility.

To measure a sensible difference between B' and D, the first part of the error function includes a simulated measurement of the simulated material represented by B' with the simple reflectance scanner used for measuring the sparse reflectance values D. For this purpose a rendering of B' under the illumination and viewing conditions of the simple reflectance scanner is computed with standard methods from the area of computer graphics and the difference of the result to D is computed. The simulated measurement requires knowledge of the internal lighting and the detectors inside of the simple reflectance scanner, which are either known by design of the instrument or can be measured.a ( )

The difference between reference and source colors in the first part can be measured using conventional color distance measures such as e.g. CIE $\Delta E^*$ or simpler measures such as L1 errors.

The difference between reference and source measure reflectance data in the first part of E(B') can be minimized, making the respective part of the target material look like the source material. The similarity of the edited BTF with the original one can also be determined to ensureand therefore physical plausibility of the result.

Weighting factors can be used to compensate for scale differences between the two different parts of error measures. The weightingw factors can be chosen by the user to put more emphasis on either part of the error compensation.

As already mentioned above the modifying or editing procedure is implemented by optimizing (i.e. minimizing the above error function (E(B')) with B' as represented by its reflection values as variables). In other words, B' or its reflection values B' have to be modified in such a way that the error function E(B') becomes minimal. This task is achieved by iteration starting with the reflection values of B as zero-order approach (B'=B).

First it is explained how to minimize the error function E(B') in the most general case, where little can be assumed about the BTFs B and B". Further below two special representations for B and B' will be discussed that are suitable for certain material classes, namely near-homogeneous, near-flat materials and automotive paint materials. Such special representations are much more compact and allow for easier optimization of error functions specifically designed for them.

Many materials are too complex to be faithfully represented by simple models so that no assumption about the internal representation of their BTFs can be made. In order to minimize the error function, according to a further important aspect of the present invention, a heuristic approach based on BTF editing operators defined in Kautz 2007 is used for modifying the BTF and thereby minimizing the error function E(B').

The BTF editing operators of Kautz 2007 basically comprise four operators which, when applied to a BTF, allow for modification of the BTF with respect to gray scaling, color change (both saturation and hue) and gloss or specularity change. Each operator comprises one parameter only. By setting these parameters to higher or lower values and applying the operators to a BTF, a desired scaling, color, or specularity (gloss) change can be performed. Using these operators the problem of minimizing the error function E(B') is considerably reduced because only a few parameters have to be estimated so as to minimize the error function.

Figure 3:
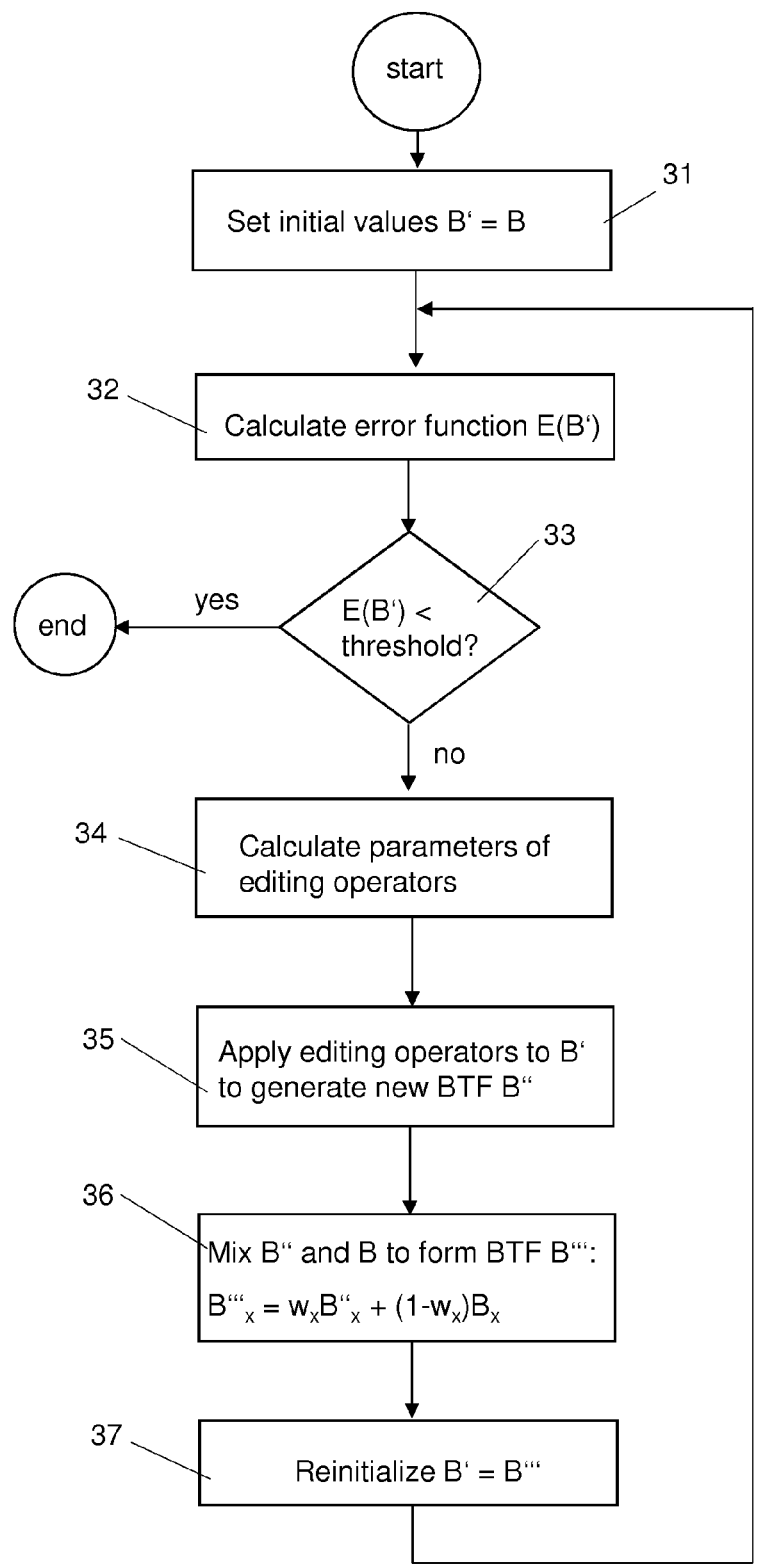
FIG. 3 is a flow diagram of a generic iteration procedure for minimizing an error function used in the method of the invention.

The iterative minimizing procedure for minimizing the error function E(B') is shown schematically in the flow diagram of FIG. 3.

Figure 2:
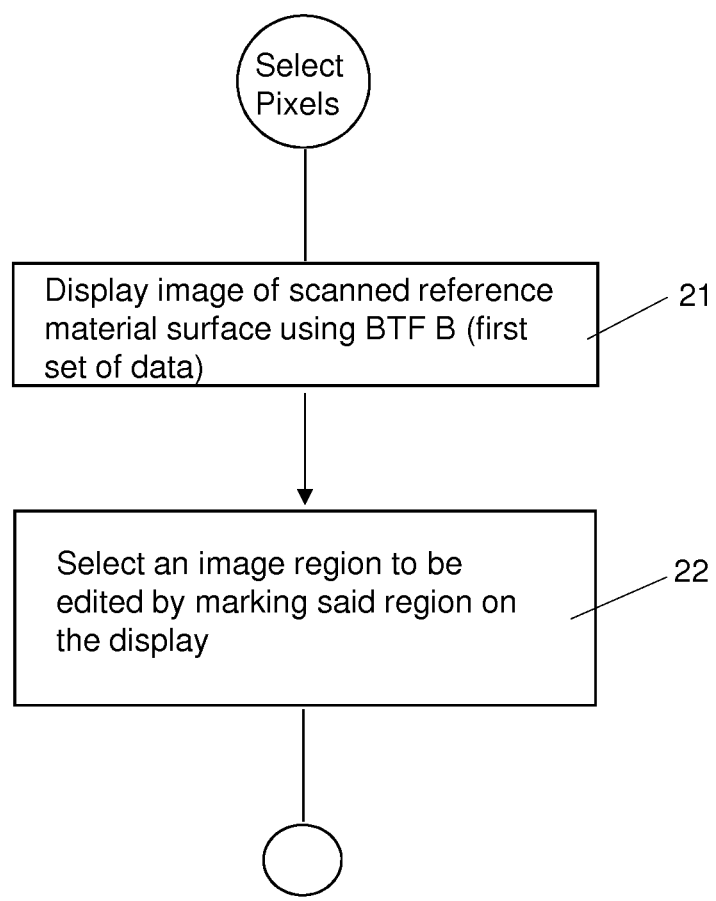
FIG. 2 is a flow diagram of one embodiment of a method for selecting pixels to be edited.

After defining the pixels x to be edited, and after computing and assigning weights $w_x$ to them as outlined in FIG. 2, an iterative algorithm is used to transfer the sparse reflectance data D into B'. At the beginning, as mentioned already, B' is initialized with the values of B (31). Then the error function E(B') is calculated (32) and its value is compared with a preset threshold value (33). The values resulting from the simulated measurement of B', $S_S$, are stored for later use. If the error function value is below the threshold value or convergence has been detected the iteration procedure is terminated. Otherwise, parameters for the Kautz et al editing operators are calculated (34) and with these parameters the Kautz et al editing operators are applied to B' to produce a new BTF B" (35). For the selected pixels x the values of this new BTF B" are than mixed with the values of the original BTF B according to $B'''_x = w_x B''_x + (1-w_x) B_x$ wherein $w_x$ are the weights assigned to the selected pixels x and $B'''_x$ are the values of an intermediate modified B''' for the pixels x (36). Then B' is reinitialized by setting B'=B''' (37). Afterwards the iteration procedure starts over at box 32 so as to iteratively modify B'.

Figure 4:
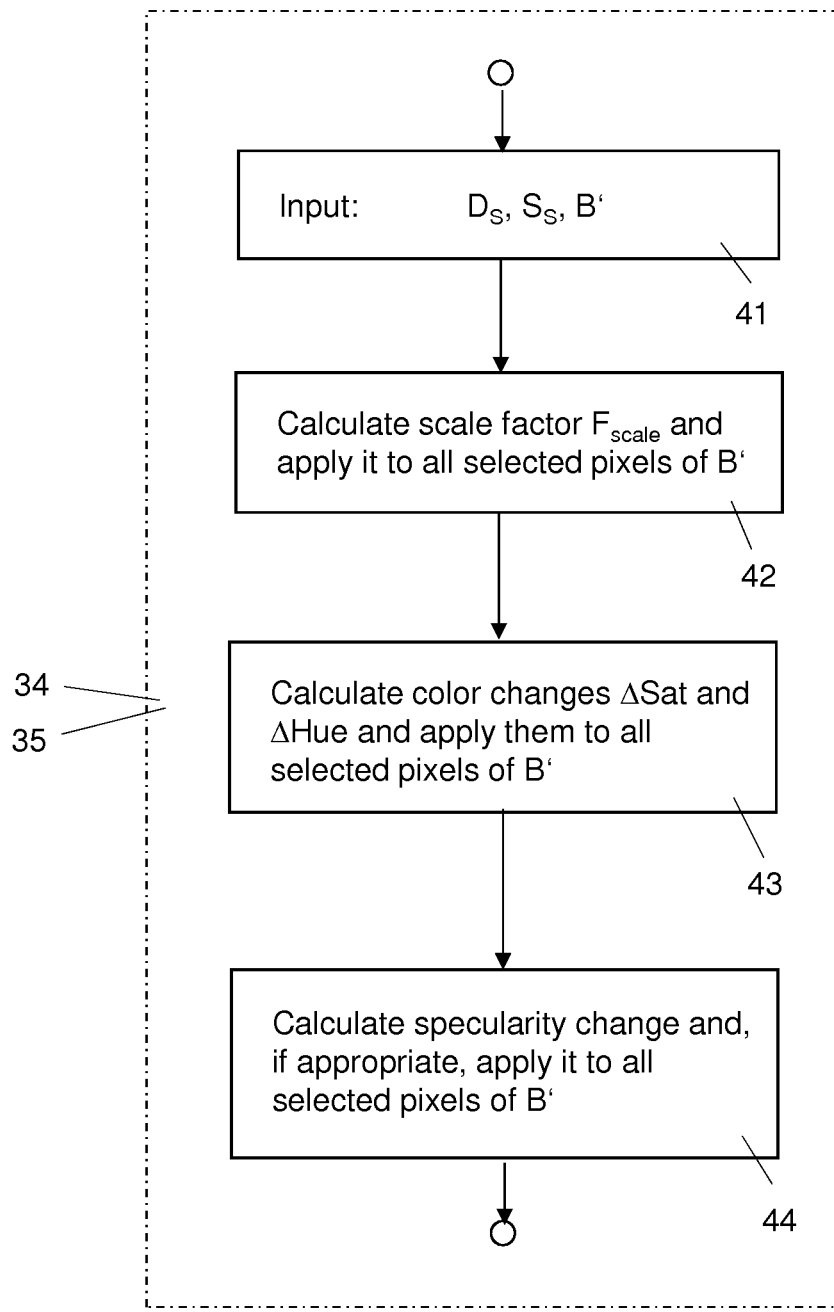
FIG. 4 is a flow diagram of a procedure for determining parameters of editing operators used in the iteration procedure shown in FIG. 3.

In the following the (sub) procedure of estimating parameters for the Kautz et al editing operators and of applying these operators to the current B' (boxes 34 and 35 of FIG. 3) will be explained in the context of the flow diagram of FIG. 4.

The (sub) procedure uses $D_S$ and the current states of B' and $S_S$ as input data (41).

At first a scaling is applied to B' by multiplying all reflectance values of B' with a scale factor $F_{scale}$ (42). Since light transport is linear, scaling all reflectance values of B' with the same scale factor is a physically plausible operation. The scale factor $F_{scale}$ is determined by comparison of the real measurements $D_s$ of the source material and the virtual measurements $S_s$ of the edited (simulated) material. Then this scale factor $F_{scale}$ is applied to the reflectance values of all selected pixels of B'.

Next a color change in both saturation and hue is calculated and a corresponding color transformation is applied to B' using the Kautz et al color change operator (43). The color change operator operates in HSV color space (hue, saturation, value) and can change the hue and saturation of BTF pixels in a physically plausible way. The color changes ΔHue and ΔSat in hue and saturation are calculated by comparison of the real measurements Ds of the source material and the virtual measurements $S_S$ of the edited material.

Hue and saturation values are calculated from the reflectance values $D_S$ and $S_S$ by known standard conversion formulas.

ΔHue and ΔSat are additive changes to be applied to the hue and saturation of B'. The color change operator from Kautz 2007 is run on all selected pixels of B' using ΔHue and ΔSat as parameters.

Figure 5:
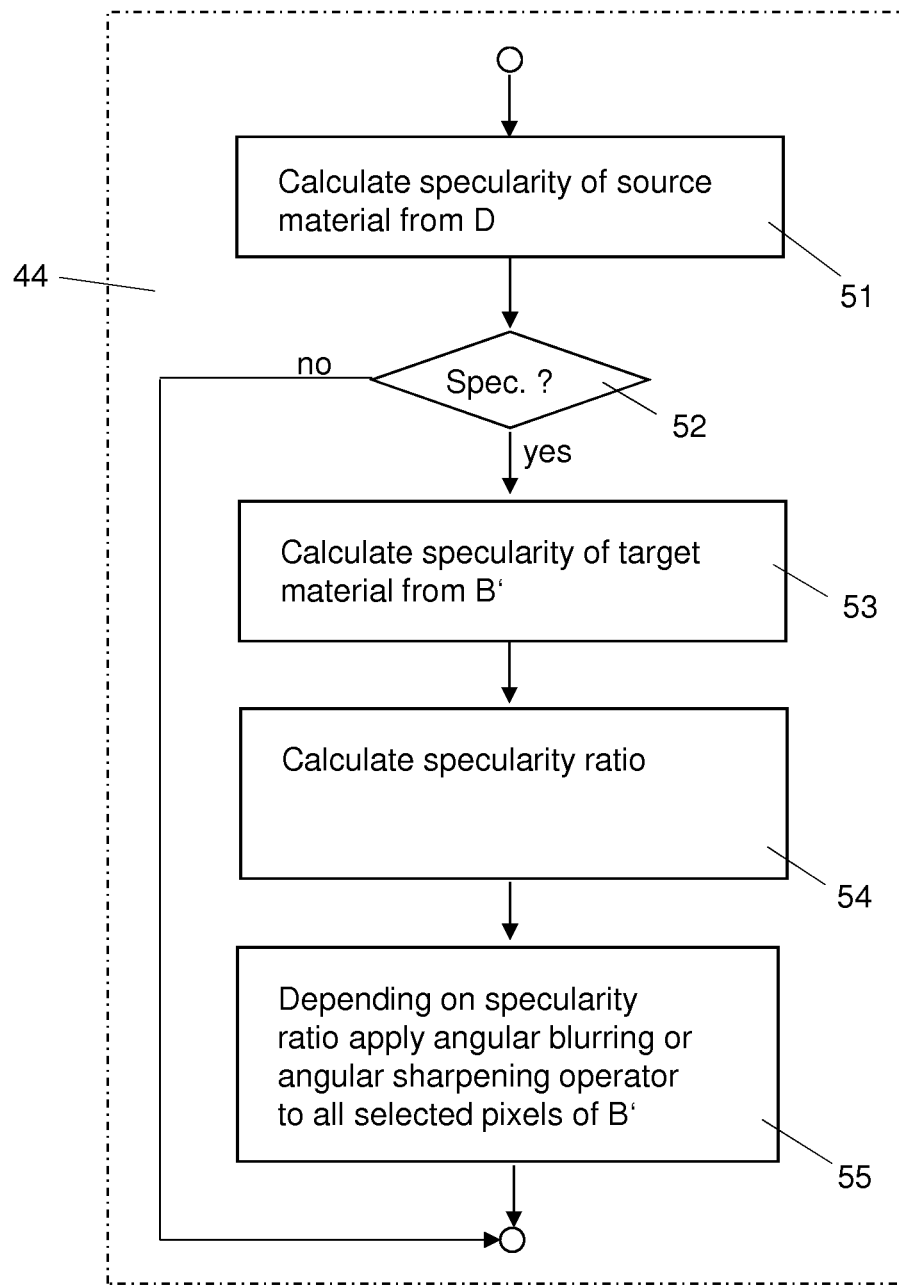
FIG. 5 is a flow diagram of a sub procedure of the procedure shown in FIG. 4.

If the simple reflectance scanner and thus the values D support for estimating the materials specularity, a specularity change from source to target material is calculated and applied to B' (44). For this purpose the angular sharpening or angular blurring operators from Kautz 2007 are used. The specularity change sub-procedure (in 44) is shown in more detail in FIG. 5.

First the specularity of the source material is determined from the sparse reflectance values D (51). For this an analytical BRDF (Bidirectional Reflectance Distribution Function) model such as the Cook-Torrance model described in Cook 1982 is fit to D by minimizing an error function which is based on the analytical BRDF model used and the set of parameter values for the model.

The error function is minimized using any standard non-linear optimization algorithm like Levenberg-Marquardt.

Otherwise, the specularity of the simulated target material is determined from the reflectance values in B' (53). For this the same analytical BRDF (Bidirectional Reflectance Distribution Function) model such as the Cook-Torrance model described in Cook1982 is fit to B' by minimizing an error function based on the analytical BRDF model used and the set of parameter values for the model. Again, the error function is minimized using any standard non-linear optimization algorithm like Levenberg-Marquardt.

In the next step (54) a ratio of the specularity parameters is calculated.

In a final step (55), either the angular blurring or the angular sharpening operator from Kautz 2007 is run on (applied to) all selected pixels of B'.

Example 2

Near-Homogenous, Near-Flat Materials

The present invention is especially suitable for certain classes of materials to be visualized; in particular the classes of near-homogeneous, near-flat materials such as paint materials, particularly automotive paint materials. In case of near-homogeneous, near-flat materials, a much more efficient representation of materials can be chosen, so that the parameters of B and B' contain already more semantic information. One example of this is the Spatially-Varying Bidirectional Reflectance Distribution Function (SVBRDF), especially in combination with a normal- or height-map to model the surface height variations. Reducing a measured BTF to such a representation is well known and not part of the present invention.

In a representation like the SVBRDF, the material is described by a BRDF model and a local coordinate frame per pixel. Since we assume that no spatial information is provided by the simple reflectance scanner, we cannot change the surface structure and therefore have to keep the local coordinate frames fixed.

To find new per-pixel parameter values for the BRDF model(s), we again employ optimization of the energy function E(B'). The difference to the generic case discussed above is, that we have much less unknown parameters for the energy function and that all parameters have a semantic, physical meaning. This makes the evaluation of the first part of the energy function very efficient. Furthermore, the second part—the physical plausibility term—is now well defined, since simple bounds can be given on the model parameters to ensure physical plausibility of the model result.

Example 3

Automotive Paint

Car paint materials typically are homogeneous up to the distortion by the sparkling due to certain pigments or flakes incorporated in the paints. Since car paints are near-homogeneous materials, the whole measured surface area of the reference material can be included into the editing process by setting P to the set of all pixels.

The BRDF of the surface is represented using the Cook-Torrance BRDF model (Cook1982) and an angular-dependent color table. The residual contains the local effects caused by the flakes, e.g. sparkling, and is represented by a specially encoded BTF.

This whole BTF is then edited in three steps: (1) new parameters for the BRDF model are calculated by matching the gray-scale reflectances with the given sparse reflectance values D; (2) the entries of color table C are recomputed to match the colors to the sparse measured reflectance values D; and (3) the colors in all pixels of the flake BTF are changed to match the edit performed on C and the angular distribution of the images is changed according to the edit. Since no spatial information is given in D, no sensible changes to the distribution of the flake effects within one image of the flake BTF are possible. More specifically in the first step, new values for the diffuse and specular coefficients as well as the roughness parameters of the Cook-Torrance model are determined using optimization. For the second step, the original color table is first warped in angular domain based on the average surface roughness change. Since the bi-angular color change of metallic paints depends on the alignment of the flake particles, and since the roughness parameter reflects the degree of misalignment, this operation corrects for the difference in flake alignment between the source and target paint. Also in the second step, a color operator is applied to the entries of the original color table to match the colors from D. This color operator depends on the color or spectral space in which the color table is defined. A typical transformation has just a few parameters. An example would be a hue and saturation change operator. In the third step, a modified flake BTF is created by applying the same angular warping and color transformation from the second step to all pixels of the flake BTF.

When these three steps have been performed, the new car paint already matches the reflectance samples in D. No further iterations as in the general case explained further above are necessary.

REFERENCES

The following references, to the extent that they provide exemplary procedural or other details supplementary to those set forth herein, are specifically incorporated herein by reference.

N. Alldrin, T. Zickler, D. Kriegman: "Photometric stereo with non-parametric and spatially-varying reflectance". In Computer Vision and Pattern Recognition. CVPR 2008. IEEE Conference on, pp. 1-8, 2008. ("Alldrin 2008")

X. An, F. Pellacini: "AppProp: Ali-Pairs Appearance-Space Edit Propagation". In ACM Transactions on Graphics, Vol. 27, No. 3, pp. 40:1-40:9, 2008. ("An 2008")

X. An, X. Tong, J. D. Denning, F. Pellacini: "AppWarp: retargeting measured materials by appearance-space warping" ACM Transactions on Graphics, Vol. 30, No. 6, pp. 147:1-147:10, 2011. ("An 2011")

R. L. Cook and K. E. Torrance: "A reflectance model for computer graphics" In ACM Transactions on Graphics, Vol. 1, Issue 1, pp. 7-24, 1982. ("Cook 1982")

K. Daubed, H. Lensch, W. Heidrich, H.-P. Seidel: "Efficient cloth modeling and rendering" In Rendering Techniques 2001, pp. 63-70, 2011. ("Daubed 2001")

M. Guthe, G. Müller, M. Schneider, R. Klein: "BTF-CIELab: A Perceptual Difference Measure for Quality Assessment and Compression of BTFs" In Computer Graphics Forum, Vol. 28, No. 1, pp. 101-113, 2009. ("Guthe 2009")

J. T. Kajiya: "The Rendering Equation" In ACM SIGGRAPH Computer Graphics, Vol. 20, No. 4, pp. 143-150, 1986 ("Kajiya 1986")

J. Kautz, S. Boulos, F. Durand: "Interactive editing and modeling of bidirectional texture functions" In ACM Transactions on Graphics, Vol. 26, No. 3, Article No. 53, 2007 ("Kautz 2007")

J. Lawrence, A. Ben-Artzi, C. DeCoro, W. Matusik, H. Pfister, R. Ramamoorthi, S. Rusinkiewicz: "Inverse shade trees for non-parametric material representation and editing" In ACM Transactions on Graphics, Vol. 25, No. 3, pp. 735-745, 2006. ("Lawrence 2006")

D. McAllister, A. Lastra, W. Heidrich: "Efficient rendering of spatial bi-directional reflectance distribution functions" In Proceedings of the ACM SIGGRAPH/EUROGRAPHICS conference on Graphics hardware, pp. 79-88, 2002. ("McAllister 2002")

M. Rump, G. Müller, R. Sarlette, D. Koch, and R. Klein: "Photo-realistic Rendering of Metallic Car Paint from Image-Based Measurements" In Computer Graphics Forum, Vol. 27, No. 2, pp. 527-536, 2008. ("Rump 2008")

M. Rump, R. Sarlette, R. Klein: "Efficient Resampling, Compression and Rendering of Metallic and Pearlescent Paint," In proceedings of Vision, Modeling, and Visualization, pages 11-18, 2009 ("Rump 2009")

S. Rusinkiewicz: "A new change of variables for efficient BRDF representation" In Rendering techniques' 98, pp. 11-22, 1998 ("Rusinkiewicz 1998")

Kun Xu, Jiaping Wang, Xin Tong, Shi-Min Hu, Baining Guo: "Edit Propagation on Bidirectional Texture Functions" In Computer Graphics Forum, Vol. 28, No. 7, pp. 1871-1877, 2009 ("Kun 2009")

What is claimed is:

1. A method of digitally generating, via a computer, data indicative of a synthesized appearance of a simulated material having physically plausible appearance attributes, with the synthesized appearance being based on a physically tangible reference material and at least one value of a selected appearance attribute of a physically tangible source material different from the reference material, comprising the steps of:
   (a) accessing, via the computer, a first set of data indicative of the values of measured appearance attributes of the reference material, with the measured appearance attributes being measured at a plurality of locations on the reference material and for a plurality of illumination directions or a plurality of viewing directions relative to each of the locations;
   (b) accessing, via the computer, a second set of data indicative of a value of at least one measured appearance attribute of the source material, wherein the appearance attribute of the source material includes at least one, but not all, of the appearance attributes being measured on the reference material; and
   (c) determining, via the computer, a third set of data indicative of the synthesized appearance of the simulated material based at least in part on data from the second set of data associated with the physically tangible source material and at least in part on data from the first set of data of measured appearance attributes of the physically tangible reference material different from that of the second set of data.

2. The method of claim 1, further comprising measuring appearance attributes of the physically tangible reference material at a plurality of locations on the reference material by illuminating each of the locations on the reference material with EM radiation in the range of near IR, UV or humanly detectable frequency spectra from a plurality of illumination directions and measuring the EM radiation reflected from or transmitted through the reference material, and determining values of the appearance attributes of the reference material based on the reflected or transmitted EM radiation to form the first set of data.

3. The method of claim 1, further comprising measuring appearance attributes of the physically tangible reference material at a plurality of locations on the reference material by illuminating each of the locations on the reference material with EM radiation in the range of near IR, UV or humanly detectable frequency spectra and measuring the EM radiation reflected from or transmitted through the reference material from a plurality of viewing directions, and determining values of the appearance attributes of the reference material based on the reflected or transmitted EM radiation to form the first set of data.

4. The method of claim 1, wherein step (c) comprises:
   (i) determining a third set of data indicative of the synthesized appearance of the simulated material based at least in part on the values of the measured appearances attributes of the source material and the values of the measured appearance attributes of the reference material,
   (ii) determining an error value consisting of
      (a) the difference between a parameter of a measured appearance attribute of the source material and the same parameter of the corresponding appearance attribute in the third set of data,
      (b) a physical plausibility value based on the difference between a parameter of a measured appearance attribute of the reference material and the same parameter of the corresponding measured appearance attribute in the third set of data and
   (iii) if the error value is greater than a predetermined threshold, then revising the determining of the third set of data indicative of the synthesized appearance of the simulated material,
   (iv) repeating steps (i) through (iii) until (i) the error value is less than the predetermined threshold or (ii) the change of the error value is less than a second, predetermined threshold.

5. The method of claim 1, wherein the first set of data constitutes a Bidirectional Texture Function (BTF), a Bi-Directional Scattering-Surface Reflectance Distribution Function (BSSRDF), Spatially Varying Bi-Directional Transmission Distribution Function (SVBTDF), or a Spatially Varying Bi-Directional Reflectance Distribution Function (SVBRDF).

6. The method of claim 1, wherein the second set of data is indicative of values of a plurality of measured appearance attributes of the source material, and wherein the appearance attributes of the source material include some, but not all, of the appearance attributes being measured on the reference material.

7. The method of claim 1, wherein the appearance attributes are selected from the group consisting of lightness, saturation, hue, gloss, specularity, distinctness of image, haze, subsurface scattering, translucency, turbidity, texture, surface height variation and normal maps.

8. The method of claim 1, wherein the appearance attribute is measurable via EM radiation in the near IR, UV or humanly detectable frequency spectra reflected from or transmitted through the reference material or the source material of the simulated material.

9. The method of claim 1, further comprising processing the third set of data to form an image representative of the synthesized appearance of the simulated material.

10. The method of claim 9, wherein the image is three dimensional.

11. The method of claim 1, further comprising processing the third set of data to print a physically tangible object having the synthesized appearance of the simulated material.

12. The method of claim 1, further comprising processing the third set of data to form a haptic display representative of the synthesized appearance of the simulated material.

13. The method of claim 1, further comprising accessing a fourth set of data indicative of standardized values of appearance attributes representative of a family of generally similar physically tangible materials of which the reference material or the source material is a member, and determining the third set of data based at least in part from data from the fourth set of data.

14. The method of claim 1, where the number of appearance attributes represented in the second set of data is less than 1% of the number of appearance attributes represented in the first set of data.

15. A data set of values of appearance attributes for a synthesized appearance of a simulated material having physically plausible appearance attributes generated by the method of claim 1.

16. An image generated from a data set of values of appearance attributes for a synthesized appearance of a simulated material having physically plausible appearance attributes generated by the method of claim 1.

17. A system for digitally generating data indicative of a synthesized appearance of a simulated material having physically plausible appearance attributes, with the synthesized appearance being based on a physically tangible reference material and at least one value of a selected appearance attribute of a physically tangible source material different from the reference material, the system comprising:

(a) memory for storing a first set of data indicative of the values of measured appearance attributes of the reference material, with the measured appearance attributes being measured at a plurality of locations on the reference material and for a plurality of illumination directions or a plurality of viewing directions relative to each of the locations;

(b) an instrument for measuring at least one appearance attribute of the source material and generating a second set of data indicative of a value of the measured appearance attribute, wherein the appearance attribute of the source material includes at least one, but not all, of the appearance attributes being measured on the reference material; and (c) a computer configured to receive the first and second sets of data and configured to determine a third set of data indicative of the synthesized appearance of the simulated material based at least in part on data from the second set of data associated with the physically tangible source material and at least in part on data from the first set of data of measured appearance attributes of the physically tangible reference material different from that of the second set of data.

18. The system of claim 17, further comprising a processor configured to receive data from the third set of data and configured to form an image representative of the synthesized appearance of the simulated material based at least in part on the data from the third set of data.

19. The system of claim 18, wherein the computer and the processor are combined in a single integral device.

20. The system of claim 17, further comprising a processor configured to receive data from the third set of data and configured to produce an object having the synthesized appearance of the simulated material based at least in part on the data from the third set of data.

21. The system of claim 17, wherein at least a portion of the memory for storing the first set of data is carried on the computer.

22. The system of claim 17, wherein the computer and the instrument are combined in a single integral device.

23. The system of claim 17, wherein data from the first and second sets of data are transmitted via media selected from the group consisting of a hardware connection, a wireless connection or a portable memory device.

24. The system of claim 17, wherein the instrument constitutes a first instrument comprising at least one source of EM radiation in the range of near IR, UV or humanly detectable frequency spectra.

25. The system of claim 24, wherein the instrument source emits the full spectra of EM radiation in the range of near IR, UV and humanly detectable frequency spectra.

26. The system of claim 24, wherein the instrument source emits a selected spectrum of EM radiation from the range of near IR, UV and humanly detectable frequency spectra.

27. The system of claim 24, wherein the first instrument further comprises at least one detector for measuring EM radiation reflected from or transmitted through the source material when illuminated by the source of EM radiation, and determining values of the appearance attributes of the source material.

28. The system of claim 24, further comprising a second instrument for measuring appearance attributes of the physically tangible reference material at a plurality of locations on the reference material by illuminating each of the locations on the reference material with EM radiation in the range of near IR, UV or humanly detectable frequency spectra from a plurality of illumination directions and measuring the EM radiation reflected from or transmitted through the reference material from a plurality of viewing directions, and determining values of the appearance attributes of the reference material based on the reflected or transmitted EM radiation for data of the first set of data.

* * * * *